United States Patent
Lampo

(10) Patent No.: US 11,027,118 B2
(45) Date of Patent: Jun. 8, 2021

(54) GEL DISPENSER FOR ELECTRODES

(71) Applicant: EMPI, INC., Vista, CA (US)

(72) Inventor: Pierre-Yves Lampo, Bretigny-sur-Morrens (CH)

(73) Assignee: DJO, LLC, Vista, CA (US)

(*) Notice: Subject to any disclaimer, the term of this patent is extended or adjusted under 35 U.S.C. 154(b) by 312 days.

(21) Appl. No.: 15/525,550

(22) PCT Filed: Nov. 9, 2015

(86) PCT No.: PCT/US2015/059755
§ 371 (c)(1),
(2) Date: May 9, 2017

(87) PCT Pub. No.: WO2016/077236
PCT Pub. Date: May 19, 2016

(65) Prior Publication Data
US 2018/0289945 A1    Oct. 11, 2018

Related U.S. Application Data

(60) Provisional application No. 62/077,809, filed on Nov. 10, 2014.

(51) Int. Cl.
*A61N 1/04* (2006.01)
(52) U.S. Cl.
CPC ......... *A61N 1/0496* (2013.01); *A61N 1/0484* (2013.01)
(58) Field of Classification Search
CPC .......................... A61N 1/0496; A61N 1/0484
See application file for complete search history.

(56) References Cited

U.S. PATENT DOCUMENTS 3,474,775 A * 10/1969 Johnson ............... A61B 5/0408
600/397
4,919,148 A * 4/1990 Muccio ............... A61N 1/0452
607/152
(Continued)

FOREIGN PATENT DOCUMENTS

WO    WO 2008/128215 A1    10/2008

OTHER PUBLICATIONS

Kuo-Kang Liu et al., "Microfluidic Systems for Biosensing", Sensors 2010, 10, 6623-6661; doi: 10.3390/s100706623, http://citeseerx.ist.psu.edu/viewdoc/download?doi=10.1.1.287.5260&rep=rep1&type=pdf, viewed on Jun. 24, 2019.*

(Continued)

*Primary Examiner* — Christopher Koharski
*Assistant Examiner* — James Moss
(74) *Attorney, Agent, or Firm* — Knobbe Martens Olson & Bear LLP

(57) ABSTRACT

A device for electrical stimulation of a user is disclosed. The device includes an electrode for applying an electrical stimulation and a gel or liquid dispensing system. The electrode is attached to a first side of a garment such that a surface of the electrode is placed in contact with a portion of a user's skin when the garment is worn by the user. The gel or liquid dispensing system is attached to the garment and configured to be actuatable to dispense a gel or liquid onto the surface of the electrode, the dispensing system having a reservoir configured to hold the gel or liquid and a fluid passageway extending from the reservoir to the surface of the electrode. The electrode may be a carbon or carbon equivalent electrode.

14 Claims, 11 Drawing Sheets

(56) References Cited

U.S. PATENT DOCUMENTS

| | | | | |
|---|---|---|---|---|
| 5,078,134 A * | 1/1992 | Heilman | ............ | A61B 5/6831 |
| | | | | 600/508 |
| 10,046,160 B1 * | 8/2018 | Kern | ............ | A61N 1/328 |
| 2001/0044573 A1 * | 11/2001 | Manoli | ............ | A61B 5/0478 |
| | | | | 600/383 |
| 2010/0030299 A1 * | 2/2010 | Covalin | ............ | A61N 1/0456 |
| | | | | 607/46 |
| 2014/0213875 A1 * | 7/2014 | Freeman | ............ | A61B 5/6839 |
| | | | | 600/386 |
| 2014/0249613 A1 * | 9/2014 | Kaib | ............ | A61B 5/0408 |
| | | | | 607/149 |
| 2016/0022981 A1 * | 1/2016 | Wingeier | ............ | A61B 5/0478 |
| | | | | 607/139 |
| 2017/0056682 A1 * | 3/2017 | Kumar | ............ | A61N 1/046 |

OTHER PUBLICATIONS

International Search Report and Written Opinion dated Jan. 29, 2016 in International Application No. PCT/US2015/059755, filed on Nov. 9, 2015.

* cited by examiner

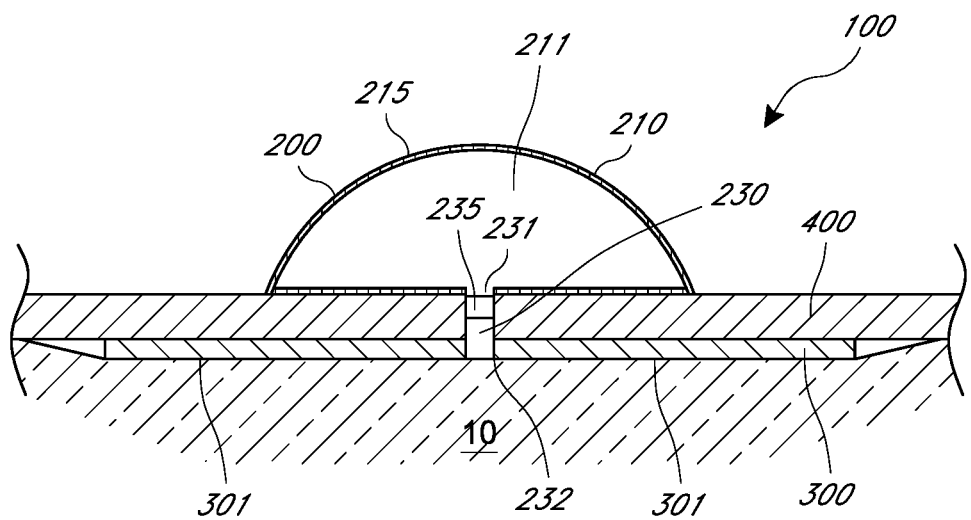
FIG. 1A
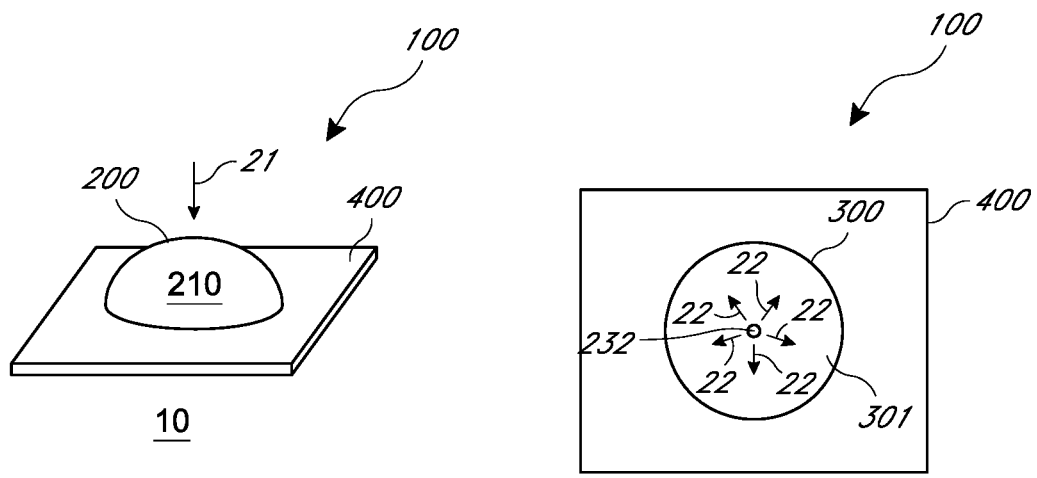
FIG. 1B
FIG. 1C

FIG. 3A
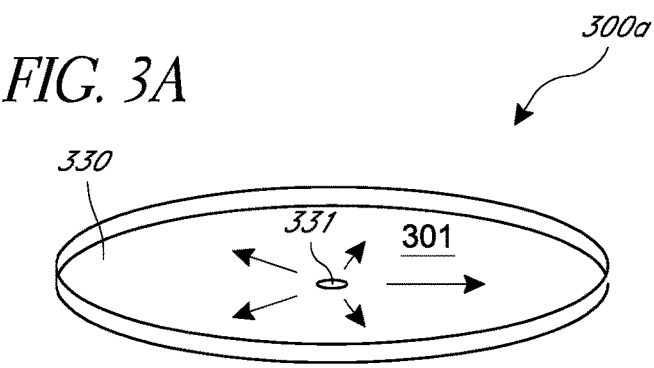
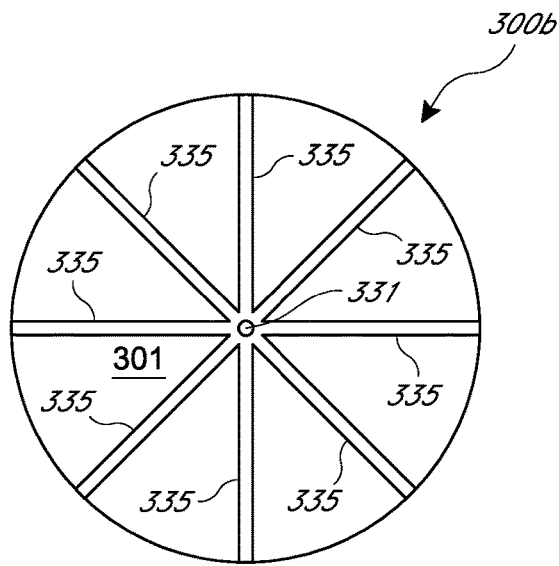
FIG. 3B
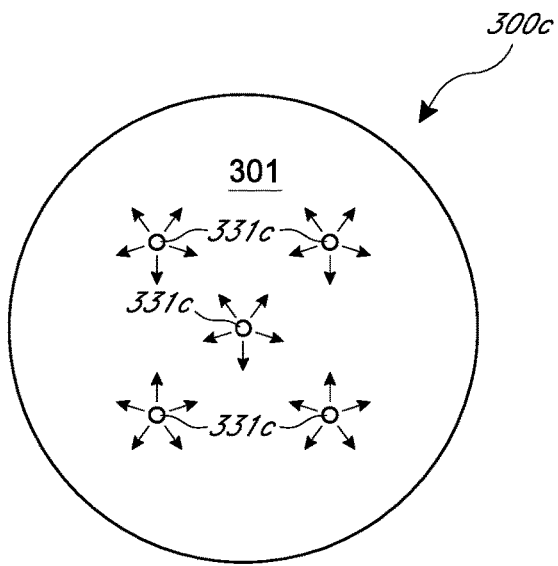
FIG. 3C
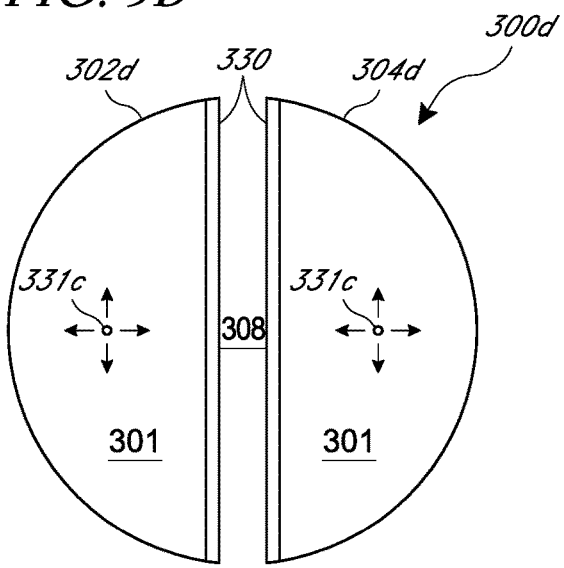
FIG. 3D
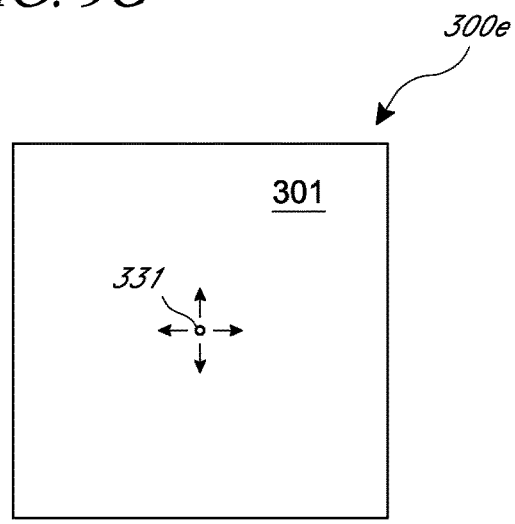
FIG. 3E

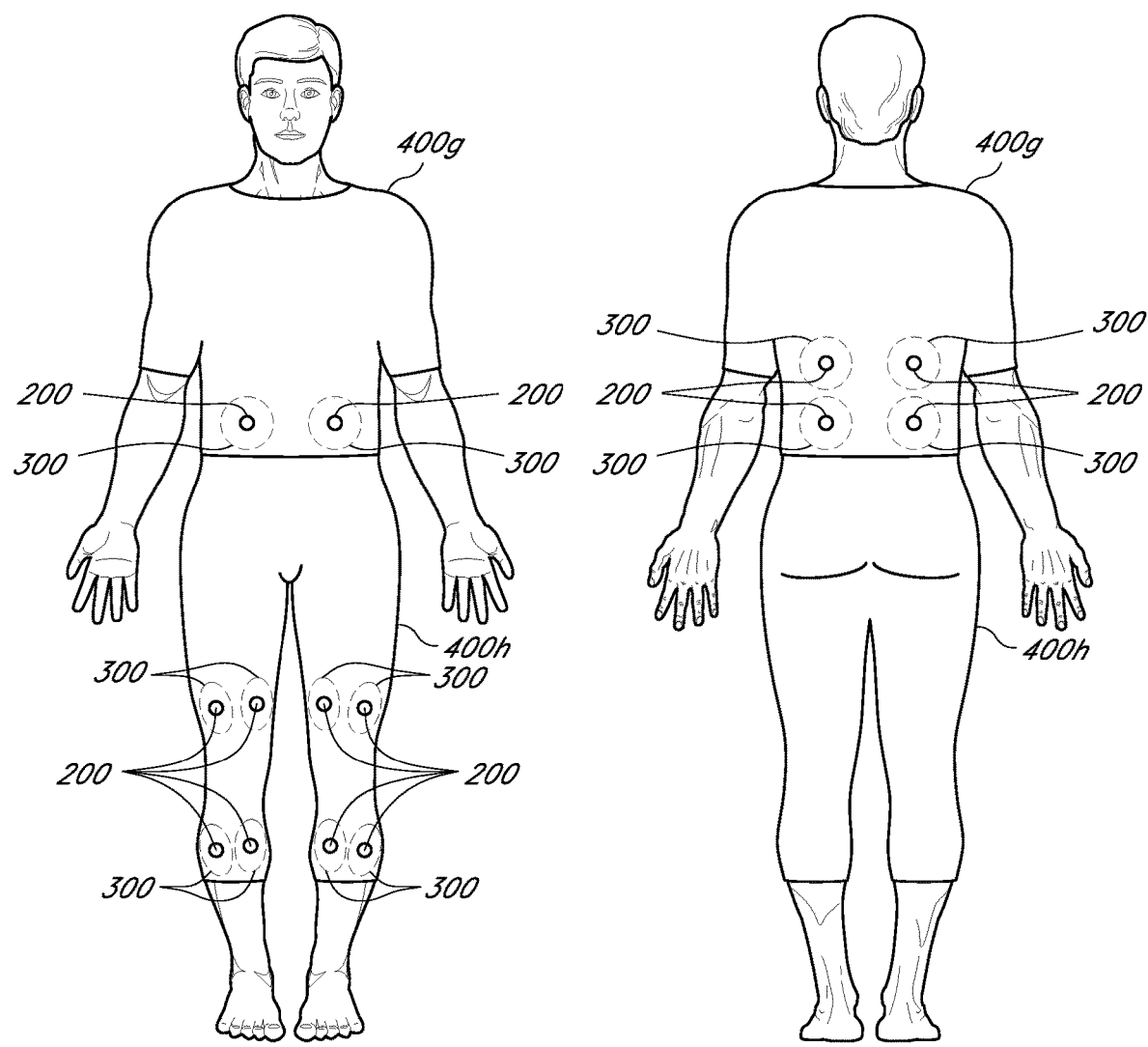
*FIG. 7E*  *FIG. 7F*

GEL DISPENSER FOR ELECTRODES

INCORPORATION BY REFERENCE TO RELATED APPLICATIONS

Any and all priority claims identified in the Application Data Sheet, or any correction thereto, are hereby incorporated by reference under 37 CFR 1.57. This application is the national phase under 35 U.S.C. § 371 of PCT International Application No. PCT/US2015/059755 which has an International Filing Date of Nov. 9, 2015, which claims the benefit of U.S. Provisional Application No. 62/077,809, filed on Nov. 10, 2014. The Each of the aforementioned applications is incorporated by reference herein in its entirety, and each is hereby expressly made a part of this specification.

BACKGROUND

This disclosure relates to electrodes for delivering an electrical stimulation therapy to a user. In particular, this disclosure relates to dry electrodes that require or are improved by the use of a conductive gel or liquid.

Many electrical stimulation devices use adhesive or sticky electrodes for delivering electrical stimulation therapy to a user. In some instances, these electrodes self-adhere to the user's body and may not require the use of any additional conductive gel or liquid. These types of electrodes are often consumable and/or disposable, that configured for a limited number of uses. Because these types of electrodes are sticky and have a relatively short use-life, they are not typically incorporated into conductive garments (in other words, garments that include built-in electrodes).

Dry electrodes, such as carbon or carbon equivalent electrodes, have been developed that are more durable and some exhibit better electrical properties than traditional adhesive electrodes. Dry electrodes may be durable, having a long use-life. These types of electrodes may be better suited for integration into conductive garments. However, dry electrodes often require or are improved by the use of a layer of conductive gel or liquid between the electrode and the user's body.

SUMMARY

The embodiments disclosed herein provide electrodes with gel dispensing systems that may be integrated into garments. Each of the described embodiments has several aspects, no single one of which is solely responsible for the disclosure's desirable attributes. Without limiting the scope of this disclosure, its more prominent features will now be briefly discussed. After considering this discussion, and particularly after reading the section entitled "Detailed Description," one will understand how the features of the embodiments described herein provide advantages over existing systems, devices, and methods.

A device for electrical stimulation of a user may include an electrode and a gel or liquid dispensing system integrated into a garment. The electrode may be attached to a first side of the garment such that a surface of the electrode is placed in contact with a portion of a user's skin when the garment is worn. The gel or liquid dispensing system may also be attached to the garment and configured to be actuatable to dispense a gel or liquid onto the surface of the electrode. The gel or liquid dispensing system may include a reservoir configured to hold the gel or liquid and a fluid passageway extending from the reservoir to the surface of the electrode. The fluid passageway may be configured to deliver the gel or liquid from the reservoir to the surface of the electrode when the dispensing system is actuated.

In some embodiments, the dispensing system is attached to a second side of the garment, the second side opposite the first side. The dispensing system may be attached to the garment at a position substantially opposite the electrode or spaced apart from the electrode. In some embodiments, the fluid passageway extends through an opening in the garment. The fluid passageway may also extend through an opening in the electrode.

In some embodiments, the device for electrical stimulation includes a valve positioned in the fluid passageway. The valve may be a one-way valve configured to allow the gel or liquid to flow in only a direction from the reservoir to the electrode. The valve may also limit flow through the fluid passageway such that flow only occurs when the gel or liquid dispensing system is actuated. The valve may be a pressure relief valve.

In some embodiments, the reservoir may be at least partially formed of a pressure deformable material and actuating the dispensing system may include applying pressure to the reservoir. In some embodiments, the reservoir is selectively attachable to the garment. That is, in some embodiments, the reservoir is removable from the garment. In some embodiments, the reservoir is refillable. The reservoir may include an input port for refilling the reservoir. In some embodiments, the reservoir is configured to receive pre-filled packets of the gel or liquid.

In some embodiments, the electrode comprises carbon. In some embodiments, the electrode is a carbon equivalent electrode. In some embodiments, the electrode is non-adhesive. In some embodiments, the electrode is a dry electrode. The electrode may be reusable. The electrode may include surface features formed on or in the surface configured to distribute the gel or liquid across the surface of the electrode. In some embodiments, the surface features are channels formed on or in the surface. In some embodiments, the channels are micro-channels. The electrode may include a barrier configured to prevent the gel or liquid from spreading beyond the electrode. The barrier may extend around a perimeter of the electrode.

In some embodiments, the electrode includes a plurality of electrodes and the fluid passageway includes a plurality of fluid passageways, each of the plurality of fluid passageways extending between the reservoir and one of the plurality of electrodes.

In some embodiments, the garment is configured in size and shape to worn on a thigh, knee, abdominal region, lower back region, shoulder, or other body part of the user.

In some embodiments, the electrical stimulation device further includes a controller electrically connected to the electrode. The controller may be configured to provide an electrical stimulation to the user via the electrode.

A method of using an electrode configured for electrical stimulation may include placing a surface of the electrode in contact with a user's skin and actuating a gel or liquid dispensing system to dispense a gel or liquid onto the surface of the electrode while the surface of the electrode is in contact with the user's skin. In some embodiments, placing the surface of the electrode in contact with a user's skin includes donning a garment wherein the electrode is embedded. In some embodiments, the gel or liquid dispensing system includes a pressure-deformable reservoir configured to hold the gel or liquid, and actuating the gel or liquid dispensing system includes applying a pressure to deform the reservoir. In some embodiments, the method further includes applying an electrical stimulation to the user via the electrode. In some embodiments, the method further includes filling or refilling the reservoir with the gel or liquid. In some embodiments, placing the surface of the electrode in contact with the user's skin is performed before actuating the gel or liquid dispensing system. The electrode may be a carbon or carbon equivalent electrode.

BRIEF DESCRIPTION OF THE DRAWINGS

The foregoing and other features of the disclosure will become more fully apparent from the following description and appended claims, taken in conjunction with the accompanying drawings, which are incorporated herein and constitute a part of the specification. Features in the drawings are not necessarily drawn to scale.

FIGS. 1A through 1C show an embodiment of an electrical stimulation device that includes an electrode and a gel dispensing system. FIG. 1A shows a cross-sectional view, FIG. 1B shows a top perspective view, and FIG. 1C shows a bottom view of the electrical stimulation device.

FIG. 2A illustrates an example of a gel dispensing system with a refillable reservoir.

FIGS. 2B and 2C illustrate an example of a gel dispensing system configured to receive gel packets.

FIG. 2D illustrates an example of a gel dispensing system that includes a removable reservoir that is selectively coupleable to a garment.

FIGS. 3A through 3G show various embodiments of electrodes configured for use with the electrostimulation devices described herein.

FIG. 3A is a perspective bottom view of an example electrode configured with an embodiment of a barrier configured to prevent gel from spreading beyond the edges of the electrode.

FIG. 3B is a bottom view of an electrode configured with an embodiment of channels for distributing the gel across the electrode.

FIG. 3C is a bottom view of an embodiment of an electrode configured with multiple openings from which gel can be dispensed onto the electrode.

FIG. 3D is a bottom view of an embodiment of an electrode configured with two distinct electrically active zones separated by a channel.

FIG. 3E is a bottom view of an embodiment of a square electrode.

FIG. 3F is an embodiment of an electrode configured with sensors for determining whether the surface has been wetted with a gel or liquid.

FIG. 3G illustrates an embodiment of an electrode with concentric electrically active zones.

FIG. 4A shows an embodiment with a gel dispensing system that is configured to dispense gel to four distinct electrodes integrated into a garment.

FIG. 4B shows an embodiment with a gel dispensing system that includes an actuatable reservoir separated from the electrode. Such an embodiment may be advantageous in that the actuatable reservoir may be positioned so as to be easily accessible while the electrode can be positioned in a comparatively inaccessible location.

FIGS. 7A through 7H show various views and embodiments of garments into which the electrical stimulation devices described throughout this disclosure may be integrated. These are provided by way of example only, and should not be limited to integration with only these exemplary types of garments.

DETAILED DESCRIPTION

Figure 2A:
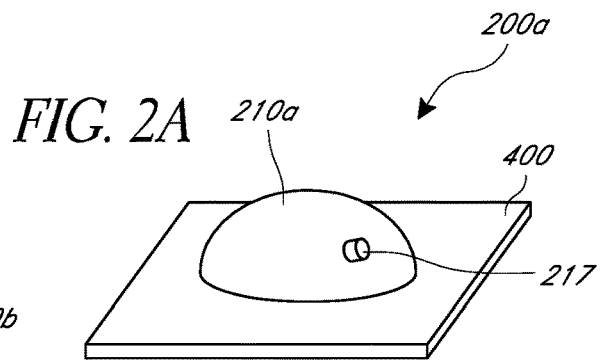
FIGS. 2A through 2D illustrate various embodiments of gel dispensing systems that can be incorporated into electrical stimulation devices.

Devices, systems, and methods are described herein for providing electrical stimulation to a user. For example, a device for providing electrical stimulation to a user may include an electrode for applying the electrical stimulation and a gel or liquid dispensing system configured to dispense gel or liquid onto the electrode. The electrode may be attached to a garment such that a surface of the electrode is placed in contact with a portion of a user's skin when the garment is worn. The gel or liquid dispensing system may also be attached to the garment and configured to be actuatable to dispense a gel or liquid onto the surface of the electrode. The dispensing system may have a reservoir configured to hold the gel or liquid and a fluid passageway extending from the reservoir to the surface of the electrode. The electrode may be a carbon or carbon equivalent electrode. Various embodiments of this and other devices will be described below in greater detail. An example method may include placing a surface of an electrode in contact with a user's skin and actuating a gel or liquid dispensing system to dispense a gel or liquid onto the surface of the electrode while the surface of the electrode is in contact with the user's skin. In some embodiments, placing the surface of the electrode in contact with the user's skin may include donning a garment wherein the electrode is embedded. The gel or liquid dispensing system may include a pressure-deformable reservoir configured to hold the gel or liquid, and actuating the gel or liquid dispensing system may include applying a pressure to deform the reservoir. Various embodiments of this and other methods will be described in greater detail below.

In the following detailed description, reference is made to the accompanying drawings. In the drawings, similar symbols and reference numbers typically identify similar components, unless context dictates otherwise. Thus, in some embodiments, part numbers may be used for similar components in multiple figures, or part numbers may vary from figure to figure. The illustrative embodiments described herein are not meant to be limiting. Other embodiments may be utilized, and other changes may be made, without departing from the spirit or scope of the subject matter presented. It will be readily understood that the aspects of the present disclosure and those illustrated in the figures, can be arranged, substituted, combined, and designed in a wide variety of different configurations by a person of ordinary skill in the art, all of which are made part of this disclosure.

Reference in the specification to "one embodiment," "an embodiment," or "in some embodiments" means that a particular feature, structure, or characteristic described in connection with the embodiment is included in at least one embodiment. Moreover, the appearance of these or similar phrases throughout the specification do not necessarily all refer to the same embodiment, nor are separate or alternative embodiments necessarily mutually exclusive. Various features are described herein which may be exhibited by some embodiments and not by others. Similarly, various requirements are described which may be requirements for some embodiments but may not be requirements for other embodiments.

FIGS. 1A through 1C show an embodiment of an electrical stimulation device 100 that includes a gel dispensing system 200 and an electrode 300. FIG. 1A shows a cross-sectional view, FIG. 1B shows a top, perspective view, and FIG. 1C shows a bottom view of the electrical stimulation device 100. The electrical stimulation device 100 may be configured as part of a garment 400, for example, as illustrated in the figures. That is, the electrical stimulation device 100 may be attached to (or selectively attachable to) the garment 400. In some embodiments, however, the electrical stimulation device 100 need not be integrated into a garment and may be a stand-alone device. FIGS. 1A through 1C illustrate only a section of the garment 400. Embodiments of garments can be configured to be worn on any body part, including, but not limited to, a user's thigh, knee, abdominal region, lower back, or shoulder, among others. In general, the garment may be used to position the electrical stimulation device 100 on the body of the user. Several example garments are shown and described in reference to FIGS. 7A through 7H below. In the illustrated embodiment of FIGS. 1A through 1C, the gel dispensing system 200 is disposed on an exterior side of the garment 400, the exterior side being the side of the garment facing away from a user's skin 10 when the garment is worn. The electrode 300 is positioned on the opposite side of the garment 400, in other words, the interior side of the garment 400, facing the user's skin 10. Thus, when the garment 400 is worn, the electrode 300 contacts the user's skin 10.

In some embodiments, the electrode 300 may be a dry electrode or a non-adhesive electrode. In some embodiments, the electrode is a carbon or carbon equivalent electrode. These types of electrodes may exhibit better electrical properties than adhesive electrodes and can be indefinitely reused. Because these types of electrodes are non-adhesive (not sticky) and durable, they can advantageously be incorporated into garments. These electrodes may require the use of (or exhibit improved efficiency and/or patient comfort when used with) a conductive liquid or gel. However, when integrated into a garment, it can be difficult to apply the gel or liquid to the electrode. If the gel or liquid is applied before the electrode is in place (in other words, before the garment is donned), the gel or liquid can be smeared or spread across the user's skin as the user dons the garment. This may create a short circuit between multiple electrodes or dissipate the gel or liquid to an inefficient or ineffective level. Applying the gel or liquid to the electrode after the garment is donned also poses difficulties. For example, the electrode may be difficult to reach. Embodiments of electrical stimulation devices, such as electrical stimulation device 100, may alleviate these difficulties as the garment can be placed on the user before the gel or liquid is applied to the electrode, and then, gel or liquid can accurately and simply be dispensed onto the electrode 300 by means of the gel dispensing system 200. Embodiments of the electrode 300 are described in greater detail below in reference to FIGS. 3A through 3G, although the electrode 300 is not limited only to the embodiments shown and described.

In general, the gel dispensing system 200 is configured to dispense a gel or liquid onto the electrode 300. Although this disclosure describes a "gel" dispensing system throughout, the disclosure is not intended to be limited to systems that dispense only gel. The gel dispensing systems described herein may be configured to dispense any liquid or gel, and especially those conductive liquids or gels that are configured for use with electrodes. As noted above, many dry electrodes, such as carbon or carbon equivalent electrodes, require the use of (or exhibit improved efficiency and/or patient comfort when used with) a conductive liquid or gel. It is these conductive liquids or gels that are intended to be distributed by the gel dispensing system. These conductive liquids or gels include, for example, hydrogels or water, among others. As will be described in greater detail below, the gel dispensing system 200 is actuatable (that is, may be acted upon or operated) to dispense the liquid or gel onto the electrode. The gel dispensing system 200 may be configured to dispense a quantity of gel or liquid sufficient to cover the electrode with a thin layer. The quantity of gel or liquid dispensed may be dependent on the size of the electrode.

In the illustrated embodiment, the gel dispensing system 200 includes a reservoir 210 and fluid passageway 230. The fluid passageway 230 may be a conduit that extends from the reservoir 210 to the electrode 300. The reservoir 210 defines an enclosed volume 211 configured to hold a quantity of the gel or liquid. In some embodiments, the reservoir 210 is configured to hold sufficient gel or liquid for multiple uses (in other words, multiple instances of dispensing gel onto the electrode 300). In some embodiments, the reservoir 210 is configured to hold sufficient gel or liquid for at least twenty uses, at least ten uses, at least five uses, or at least a single use. Moreover, as will be described below, in some embodiments, the reservoir 210 is configured to be refillable, such that additional gel or liquid can be added to the reservoir 210 after the liquid or gel has been depleted, and/or replaceable.

In the example shown in FIGS. 1A through 1C, the reservoir 210 is configured in the shape of a bubble. An upper portion of the bubble may include a pressure deformable surface 215. The pressure deformable surface 215 may be made from a thin plastic or rubber material, or any other suitable material, that deforms under pressure. For example, the pressure deformable surface 215 may be configured such that it may deform when pressure is applied by a user's finger or hand. As the pressure deformable surface 215 deforms under the applied pressure, the enclosed volume 211 is reduced, causing the gel or liquid contained in the reservoir 210 to be expelled from the reservoir 210 through the fluid passageway 230. The liquid or gel flows through the fluid passageway 230 to the electrode 300. As the liquid or gel exits the fluid passageway 230 it is redirected by the user's skin 10 and spreads across the electrode 300 and the user's skin 10, forming a conductive layer therebetween. In the illustrated embodiment of FIGS. 1A through 1C, the fluid passageway 230 dispenses the gel or liquid onto the electrode via an outlet 232 positioned in the center of the electrode 300 (see FIG. 1C), and the gel or liquid spreads in the direction of the arrows 22 across the surface of the skin 10 facing surface 301 of the electrode 300. Thus, in the embodiment shown, the gel dispensing system 200 is configured to be actuated (in other words, configured to dispense gel or liquid) by applying pressure to the bubble-shaped reservoir 210. Pressure may be applied, for example, in the direction of the arrow 21 illustrated in FIG. 1B. Pressure may also be applied in other ways, for example, by pinching the reservoir 210. Additional features and embodiments of the reservoir 210 are shown and described below in reference to FIGS. 2A through 2D, although other embodiments and modifications beyond those illustrated and described are also possible and within the scope of this disclosure.

As shown in FIG. 1A, the fluid passageway 230 extends between the enclosed volume 211 of the reservoir 210 and the electrode 300. The fluid passageway 230 has an inlet 231 and an outlet 232. In the embodiment shown, the fluid passageway 230 is formed as a hole extending through the garment 400 and the electrode 300, and thus, a portion of the garment 400 and the electrode 300 form the fluid passageway 230. However, in some embodiments, the fluid passageway 230 is formed by a tube or other conduit extending from the inlet 231 to the outlet 232. Further, while the reservoir 210 is shown positioned on the garment 400 substantially opposite the electrode 300, this need not always be the case. Thus, where the reservoir 210 and the electrode 300 are spatially separated on the garment 400, the length, route, and shape of the fluid passageway 230 may be modified so as to extend between the reservoir 210 and the electrode 300 (see, for example, FIG. 4B). In some embodiments, the fluid passageway extends across the exterior surface of the garment 400, across the interior surface of the garment 400, through the garment 400, or any combination thereof.

In some embodiments, including that of FIGS. 1A and 1C, the fluid passageway 230 includes a valve 235 positioned between the inlet 231 and the outlet 232. The valve 235 may be a one-way valve configured to limit the flow of gel or liquid through the fluid passageway 230 to only a single direction from the reservoir 210 to the electrode. In some embodiments, the valve 235 may be omitted. In some embodiments, the valve 235 is configured to limit flow through the fluid passageway 230 to only when the gel dispensing system 200 is actuated. The valve 235 may be configured as a pressure relief valve.

FIGS. 2A through 2D illustrate various embodiments of gel dispensing systems that can be incorporated into electrical stimulation devices. These embodiments, as well as modifications and/or combinations thereof, may be incorporated into the electrical stimulation device 100 described above. Further, this disclosure is not intended to be limited to the disclosed embodiments. In general, similarly numbered elements in FIGS. 2A through 2D correspond to similar structures of the electrical stimulation device 100.

FIG. 2A illustrates an example of a gel dispensing system 200a with a refillable reservoir 210a. The reservoir 210a includes an inlet port 217 through which gel or liquid can be added to the reservoir 210a. In some embodiments, the inlet port 217 is adapted to selectively connect to a gel or liquid source to refill the reservoir. In some embodiments, the inlet port 217 is configured to receive a needle or syringe, through which gel or liquid can be injected into the reservoir 210a. The inlet port 217 may include a one-way valve, so that gel or liquid can only flow in a single direction (into) the reservoir 210a.

Figure 2B:
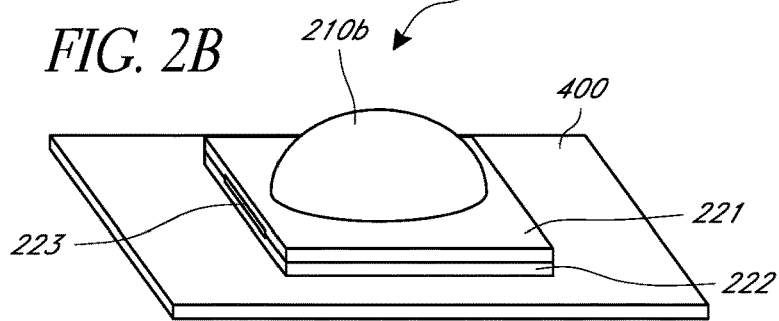
Figure 2C:
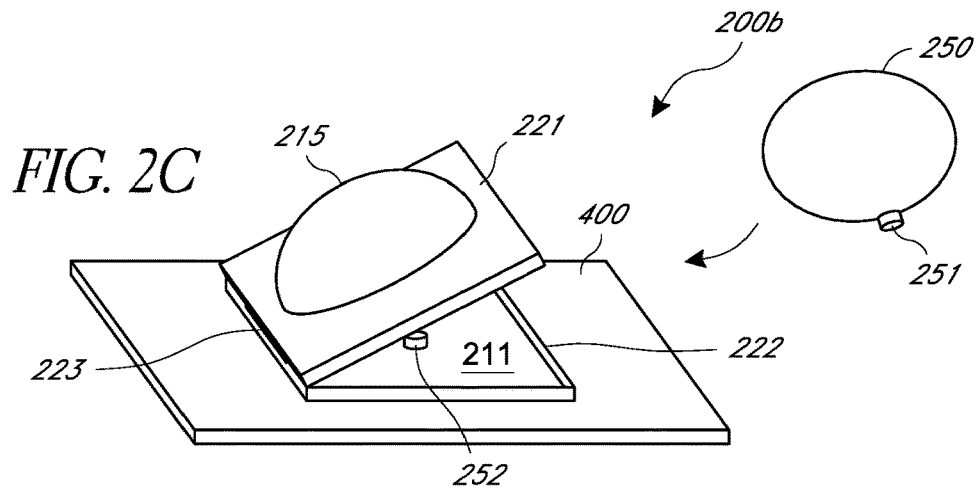

FIGS. 2B and 2C illustrate an example of a gel dispensing system 200b configured to receive gel packets 250. A reservoir 210b can be configured to have a closed position, for example, as shown in FIG. 2B, and an open position, for example, as shown in FIG. 2C. In the illustrated embodiment, the reservoir 210b includes a fixed base portion 222 attached to a moveable upper portion 221 by a hinge 223. The upper portion 221 rotates about the hinge 223 to move the reservoir 210b from the closed position to the open position and vice versa. The upper portion 221 may include a pressure deformable surface 215, such that the gel dispensing system 200b can be actuated as described above. As shown in FIG. 2C, in the open position, the reservoir 210b can receive one or more gel packets 250. A gel packet 250 may contain a quantity of gel or liquid that can be inserted into the reservoir 210b. In some embodiments, the gel packet 250 comprises a quantity of gel or liquid contained in a flexible plastic casing. The gel packet 250 may also include an outlet port 251. In some embodiments, the outlet port 251 of the gel packet 250 is configured to mate with a corresponding port 252 in the interior volume 211 of the reservoir 210b. In some embodiments, the outlet port 252 and the corresponding port 252 may be omitted. In some embodiments, pressure applied to the pressure deformable surface 215 ruptures the gel packet 250 releasing the gel or liquid within the interior volume 211 of the reservoir 210b. A gel packet 250 can be configured to hold sufficient gel or liquid for a single use or for multiple uses. In some embodiments, the gel dispensing system 200b is configured to accept different gel packets 250, containing different types or quantities of gels or liquids. Thus, a user may easily select a gel packet that corresponds with a particular use. In some embodiments, the gel packets 250 are disposable. Other methods and systems for receiving replaceable gel packets 250 are also possible and within the scope of this disclosure.

Figure 2D:
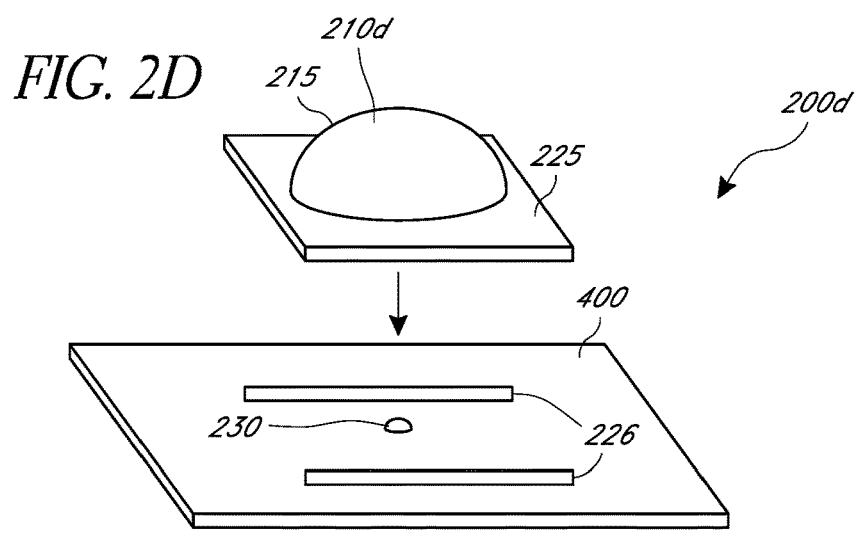

FIG. 2D illustrates an example of a gel dispensing system 200d that includes a removable reservoir 210d that is selectively coupleable to a garment 400. The removable reservoir 210d may be substantially similar to the reservoir 200 described above, although, the removable reservoir 210d is configured to be removable and selectively coupleable to the garment 400. In the illustrated embodiment, the removable reservoir 210d is configured with a base portion 225. The base portion 225 may be configured to be received in corresponding engagement structures 226 mounted on the garment 400. The engagement between the base portion 225 and the engagement structures 226 may include rail-in-groove features, snaps, clasps, or other mechanical fasteners, hook and loop, magnets, or other suitable features. The engagement structures 226 position the reservoir 210d such that an outlet of the reservoir is aligned with the fluid passageway 230, in the illustrated embodiment, the reservoir 210d includes a pressure deformable surface 215 such that the gel dispensing system 200d can be actuated as described above. The gel dispensing system 200d may be configured such that the engagement structures 226 can receive a plurality of different removable reservoirs 210d. Thus, a user may select a reservoir 210d containing a liquid or gel well suited for a particular application or replace an empty reservoir with a filled one.

FIGS. 3A through 3G show various embodiments of electrodes configured for use with the electrical stimulation devices described herein. These embodiments, as well as modifications and combinations thereof, may be incorporated into any electrical stimulation device, including the electrical stimulation device 100. Moreover, this disclosure is not intended to be limited to any of the disclosed embodiments, which are provided by way of example only. Each of the electrodes described below may be a dry or non-adhesive type electrode, such as the carbon or carbon equivalent electrodes described above.

FIG. 3A is a perspective bottom view of an example electrode 300a that includes a barrier 330 configured to prevent gel or liquid from spreading beyond the edges of the electrode 300a. The barrier 330 may contain (or substantially contain) gel or liquid on the surface of the electrode and/or prevent (or help prevent) gel or liquid from spreading to other electrodes, thus preventing a short circuit between multiple electrodes. In some embodiments, the barrier 330 may extend entirely around the peripheral edge of the electrode 300*a*. In some embodiments, the barrier 330 comprises a rigid wall configured to contain the gel or liquid. In some embodiments, the barrier 330 may be a micro-barrier. In some embodiments, the barrier 330 comprises a channel configured to contain the excess gel or liquid. In some embodiments, the barrier 330 may be formed of or include an absorbent material, for example, sponge or open cell foam. Thus, the barrier 330 may be configured to absorb excess gel or liquid. In the illustrated embodiment, the electrode 300*a* includes an opening 331 positioned in the center of the skin facing surface 301 through which the gel or liquid is received. The gel or liquid spreads in the direction of the arrows and is stopped (or substantially stopped) from spreading by the barrier 330. In some embodiments, the barrier 330 may be omitted.

FIG. 3B is a bottom view of an electrode 300*b* configured with an embodiment of channels 335 for distributing the gel or liquid across the surface 301 of the electrode 300*b*. In the illustrated embodiment, the channels 335 are formed extending radially from the opening 331. In some embodiments, the channels 335 comprise grooves in the surface 301. In some embodiments, the channels 335 may be formed between ridges extending from the surface 301. In some embodiments, the channels 335 are micro-channels and are sufficiently small so as to move the gel or liquid via capillary action. In the illustrated embodiment, the channels 335 are arranged in a spoked pattern, however, other designs are possible, including branching patterns, circular patterns, curved patterns, spiral patterns, etc. The number and configuration of the channels 335 can be implemented in a wide variety of ways that will be apparent to one of skill in the art.

FIG. 3C is a bottom view of an embodiment of an electrode 300*c* configured with multiple openings 331*c* from which gel or liquid can be dispensed onto the electrode 300*c*. The number and arrangement of the multiple openings 331*c* can be selected from among a variety of ways that will be apparent to one of skill in the art. In general, each of the multiple openings 331*c* are fed gel or liquid by individual fluid passageways or individual branches of a fluid passageway. The multiple openings 331*c* can be arranged on the skin facing surface 301 so as to help ensure an even and complete coverage of the surface 301 with the gel or liquid.

FIG. 3D is a bottom view of an embodiment of an electrode 300*d* configured with two distinct electrically active zones 302*d*, 304*d* separated by a channel 308. Each of the electrically active zones 302*d*, 304*d* may also include a barrier 330 configured to prevent gel or liquid from being dispensed into the channel 308. This may help prevent a short circuit between the two electrically active zones 302*d*, 304*d*. While two electrically active zones are shown in the illustrated embodiment, other numbers (as well as their size, shape, and arrangement) are possible. For example, an electrode may include three, four, five, or more electrically active zones.

FIG. 3E is a bottom view of an embodiment of a square electrode 300*e*. Although the electrode 300*e* is illustrated with a square shape and many of the other electrodes shown in the figures are illustrated with a circular shape, suitable electrodes for use with the devices of the present disclosure are not limited to those shapes. In some embodiments, the shape of the electrode is configured to for use on a specific body part. Various shapes for the electrode will be apparent to those skilled in the art and are each within the scope of this disclosure.

Figure 3F:
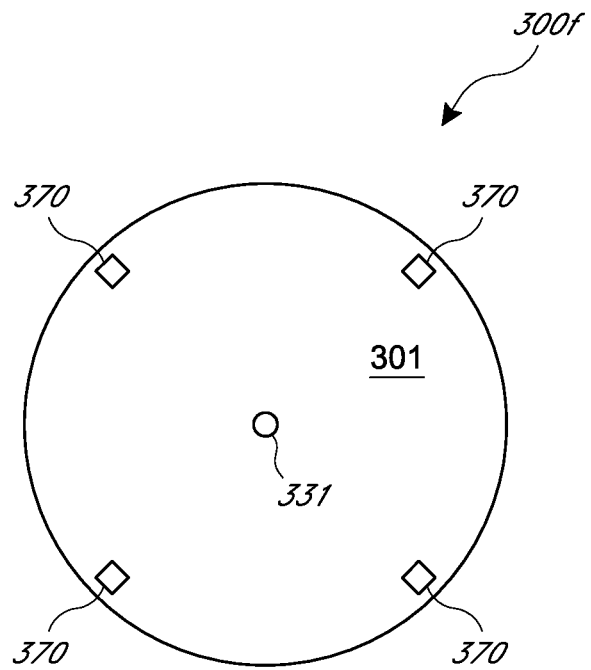

FIG. 3F is an embodiment of an electrode 300*f* configured with sensors 370 for determining whether the surface 301 is wetted by the gel or liquid. Although the electrode 300*f* is illustrated with four sensors 370, greater or fewer numbers of sensors 370 may be used. In some embodiments, the sensors 370 are positioned at the peripheral edge of the surface 301 so as to determine whether the gel or liquid has reached the edge. In some embodiments, the sensors 370 are connected to a controller. The controller may provide an alert to the user if the electrode is determined to be insufficiently wetted or be used to automate dispensing of gel or liquid onto the electrode as in the embodiment of FIG. 5, described below.

Figure 3G:
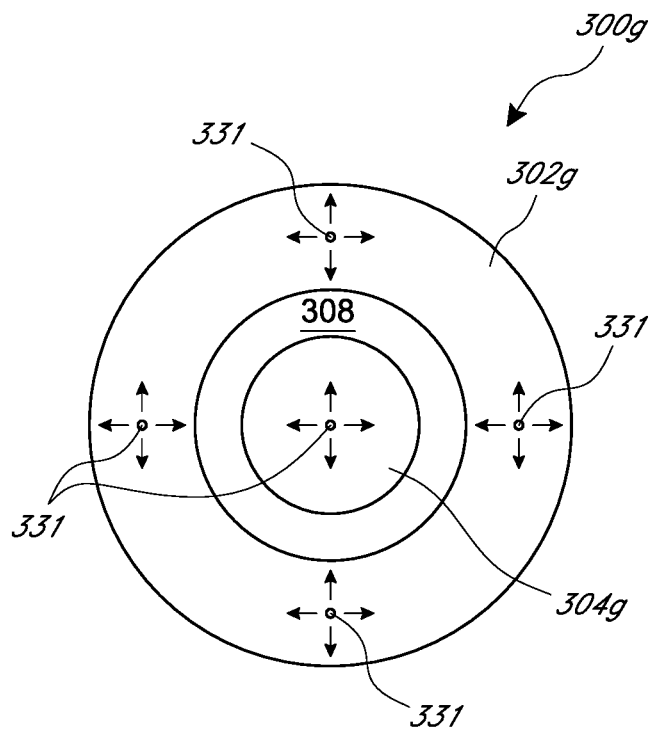

FIG. 3G illustrates an embodiment of an electrode 300*g* with concentric electrically active zones 302*g*, 304*g* separated by a channel 308. As in the embodiment of FIG. 3D, the electrically active zones 302*g*, 304*g* may include a barrier to prevent gel or liquid from entering the channel 308 and causing a short circuit between the electrically active zones.

Figure 4A:
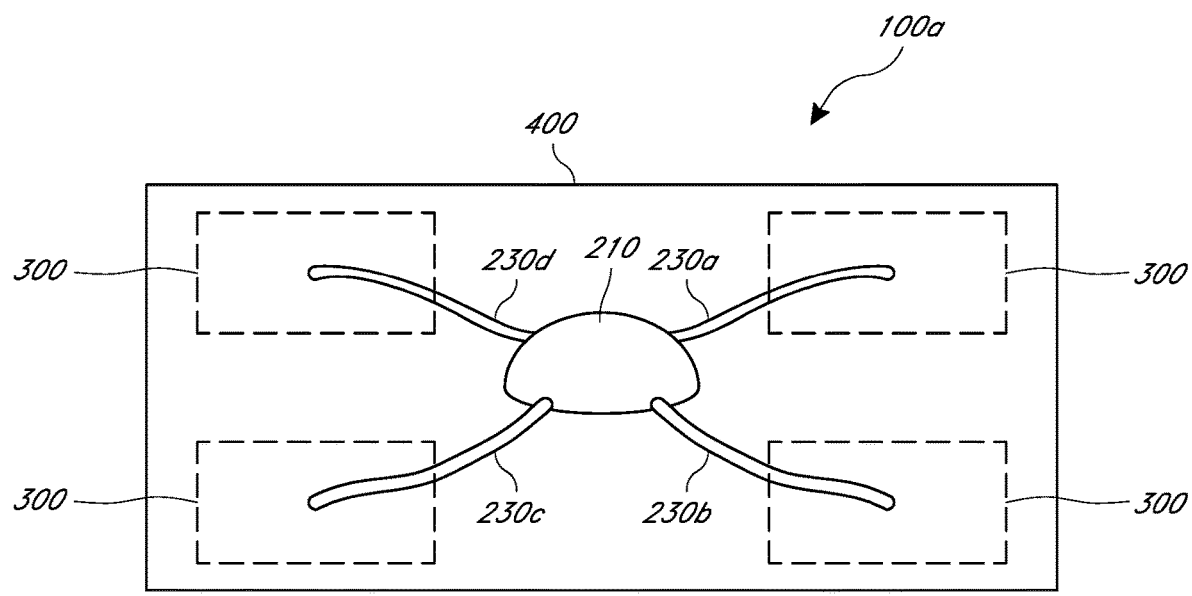
FIGS. 4A and 4B show various additional arrangements of gel dispensing systems and electrodes.

FIG. 4A shows an embodiment of an electrical stimulation device 100*a* with a gel dispensing system that is configured to dispense gel to four distinct electrodes 300 integrated into a garment 400. In the figure, only a portion of the garment 400 is shown. The gel dispensing system includes a reservoir 210 for holding a quantity of gel or liquid as described above. The reservoir 210 may include pressure deformable surface so as to be actuatable to dispense the gel or liquid. Other actuation methods are also possible and within the scope of this disclosure. In the illustrated embodiment, the gel dispensing system 200*a* includes four fluid passageways 230*a*, 230*b*, 230*c*, 230*d*, each leading to one of the four electrodes 300. The electrodes 300 are illustrated with dashed lines to represent that they may be located on the opposite side of the garment 400. In some embodiments, a gel dispensing system may include other numbers of fluid passageways and electrodes. In some embodiments, a gel dispensing system may include a single fluid passageway that branches to connect to each of the electrodes. The fluid passageways may be configured as tubes or other conduits. The tubes or conduits may be flexible. In some embodiments, the fluid passageways extend on an exterior surface of the garment, an interior surface of the garment, through the garment, or any combination thereof. In some embodiments, each electrode includes an individual and corresponding reservoir.

Figure 4B:
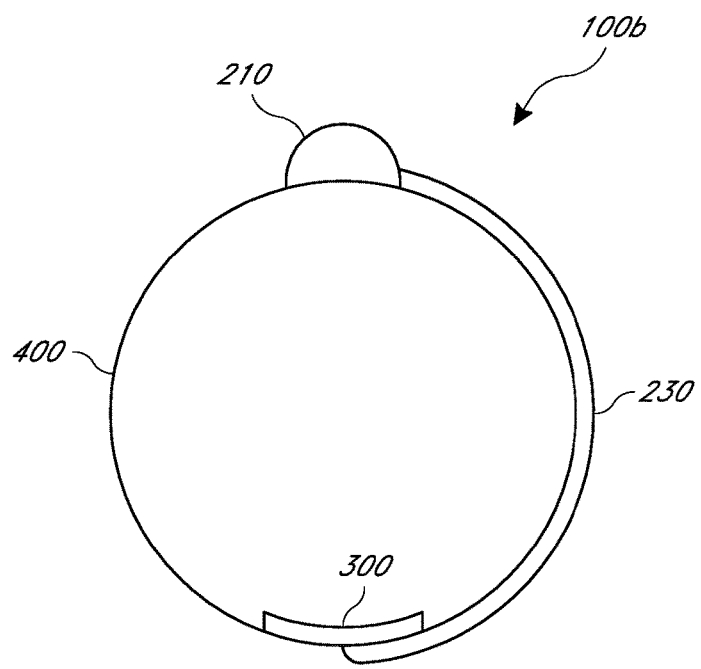

FIG. 4B shows a cross-sectional view of an embodiment of an electrical stimulation device 100*b* with a gel dispensing system that includes an actuatable reservoir 210 separated from the electrode 300. Such an embodiment may be advantageous in that the actuatable reservoir may be positioned so as to be easily accessible while the electrode can be positioned in a comparatively inaccessible location. In the illustrated embodiment, the garment 400 is illustrated as circular so as to wrap around a portion of a user's body. For example, the garment 400 may be wrapped around a user's thigh, arm, or abdomen. As shown, the reservoir 210 may be separated from the electrode 300. For example, the reservoir 210 may be located on the garment 400 so as to be positioned on the front of a user's body part and the electrode 300 may be located on the back of the user's body part. The reservoir 210 is connected to the electrode by a fluid passageway. In some embodiments, the fluid passageway extends on an exterior surface of the garment, an interior surface of the garment, through the garment, or any combination thereof. The reservoir 210 may be actuatable so as to dispense gel or liquid on the electrode 300. In some embodiments, the reservoir is positioned so as to be easily accessible such that the user can easily reach the actuation mechanism (for example, a reservoir with a pressure deformable surface) to dispense gel onto an electrode that may be located in a less accessible region. For example, the actuation mechanism may be positioned on the garment over the user's stomach (which is easily accessible by hand) and the electrode may be positioned on the user's back (which is less accessible by hand). Other locations and arrangements of the actuation mechanism and the electrode are possible.

Figure 5:
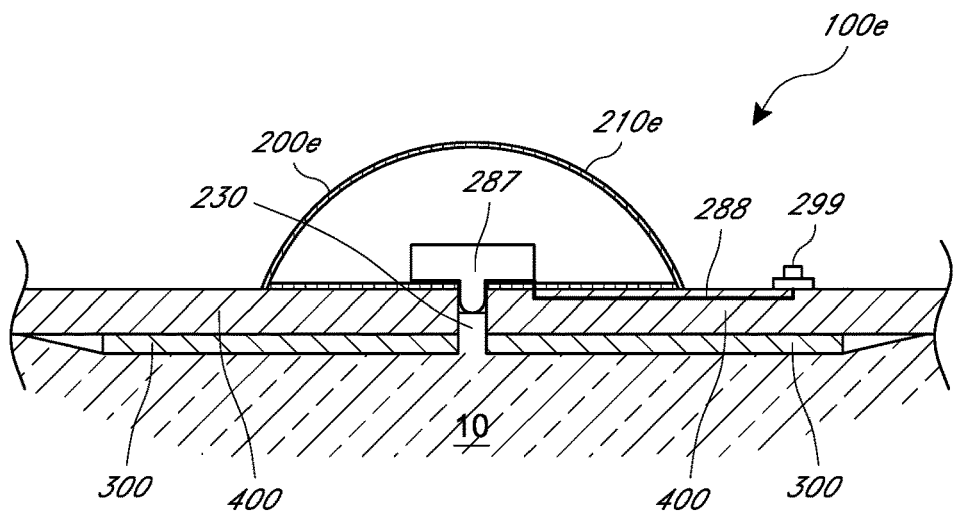
FIG. 5 illustrates a cross-sectional view of an embodiment of an electrical stimulation device that includes a gel dispensing system having an electrically operated pump for dispensing gel onto an electrode.
Figure 6A:
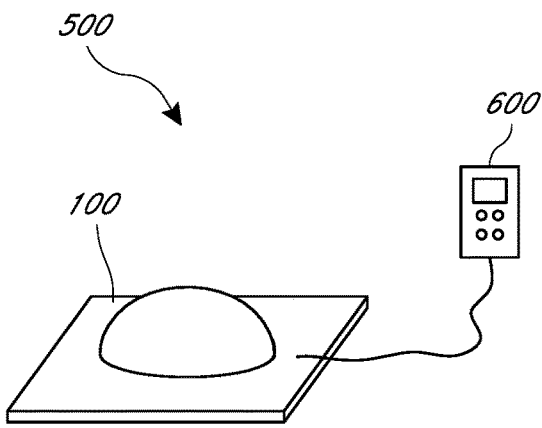
FIGS. 6A and 6B show examples of an electrical stimulation system including an electrical stimulation device connected to a controller for providing an electrical stimulation therapy.

FIG. 5 illustrates a cross-sectional view of an embodiment an electrical stimulation device 100e that includes a gel dispensing system 200e having an electrically operated pump 287 for dispensing gel or liquid onto an electrode 300. The electrical stimulation device 100e may include many features that are substantially similar to those of the electrical stimulation device 100 discussed above. For example, the fluid passageway 230, electrode 300, and garment 400 may be substantially similar to those previously discussed. The electrical stimulation device 100e may include a reservoir 210e that is configured to hold a quantity of a gel or liquid. In some embodiments, the reservoir 210e may be made from a substantially rigid material. The gel dispensing system 200e includes an electrically operated pump 287. The pump 287 is configured to move gel or liquid from the reservoir 210e through fluid passageway 230 to the electrode 300. In some embodiments, the pump 287 is located within the reservoir 210e. In some embodiments, the pump 287 is located within the fluid passageway 230. The pump 287 may be a micro pump. The pump 287 may be connected via wires 288 (or other methods for providing an electrical connection) to a power source and an activation mechanism. The wires 288 may be embedded into or extend across the exterior or interior surface of the garment. In some embodiments, the power source and activation mechanism features are included in the electrical stimulation device 100e, while, in other embodiments, these features are included on a separate electronic controller that is connected to the electrical stimulation device 100e (for example, as shown in FIG. 6A below). The activation mechanism may be a button 299. In some embodiments, pressing the button 299 causes the pump 287 to dispense a predetermined quantity of gel or liquid onto the electrode 300.

Figure 6B:
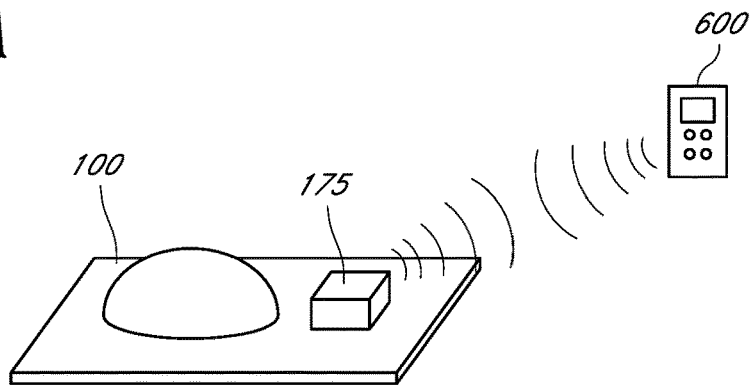

FIGS. 6A and 6B show examples of an electrical stimulation system 500 including an electrical stimulation device 100 connected to a controller 600. The controller 600 may be configured for providing an electrical stimulation therapy to the user by through one or more electrical stimulation devices 100. As shown in FIG. 6A, in some embodiments, the electrical stimulation device 100 may be connected via wires to the controller 600. As shown in FIG. 6B, in some embodiments, the electrical stimulation device 100 may be connected wirelessly to the controller 600. In these embodiments, the electrical stimulation device 100 may include circuitry 175, for establishing a wireless connection, communicating with the controller 600, and providing a power source for supplying electrical stimulation signals to the electrode, among other features. In some embodiments, the controller 600 is connected to sensors positioned on the electrode (such as those shown in FIG. 3F). The controller 600 can receive data from the sensors and determine whether the electrode has been wetted with a gel or liquid. The controller 600 may then prompt the user to wet the electrode, or, in embodiments that include an electrical pump (as in FIG. 5) the controller 600 may operate the pump to wet the electrode. Additionally, the controller 600 may include features which allow a user to select and control an electrotherapy program.

FIGS. 7A through 7H show various embodiments of garments into which the electrical stimulation devices described throughout this disclosure may be integrated. These are provided by way of example only, and should not be limited into integration with only these exemplary types of garments. One of skill in the art will appreciate that the electrical stimulation devices described herein can be integrated into a wide variety of garments other than those shown and illustrated in the figures.

In general, the garments are constructed of a non-conductive fabric and are shaped for use on a particular body part as shown in the examples described below. The garment may include one or more electrodes for delivering an electrical stimulation to a user. The garment may include one or more gel dispensing systems for dispensing gel onto the electrodes. In some embodiments, the garment may be configured to fully surround a body part. In some embodiments, the garment may include one or more straps, latches, or other closure mechanisms for securing the garment to the body part. In some embodiments, the garment may be configured to provide additional benefits or features beyond simply positioning the electrodes on the user's body. For example, the garment may be configured to provide compression to a body part. As another example, the garment may include features for bracing and/or supporting a body part. In some embodiments, the garment may provide a layer of insulation between the electrode and the gel-dispensing system. In some embodiments, the garment may include an integrated controller and/or power source which is attached to the electrodes via wires embedded into the garment. In some embodiments, the garment may include an electrical connector for connecting to an external controller and/or power source.

Figures 7A, 7B:
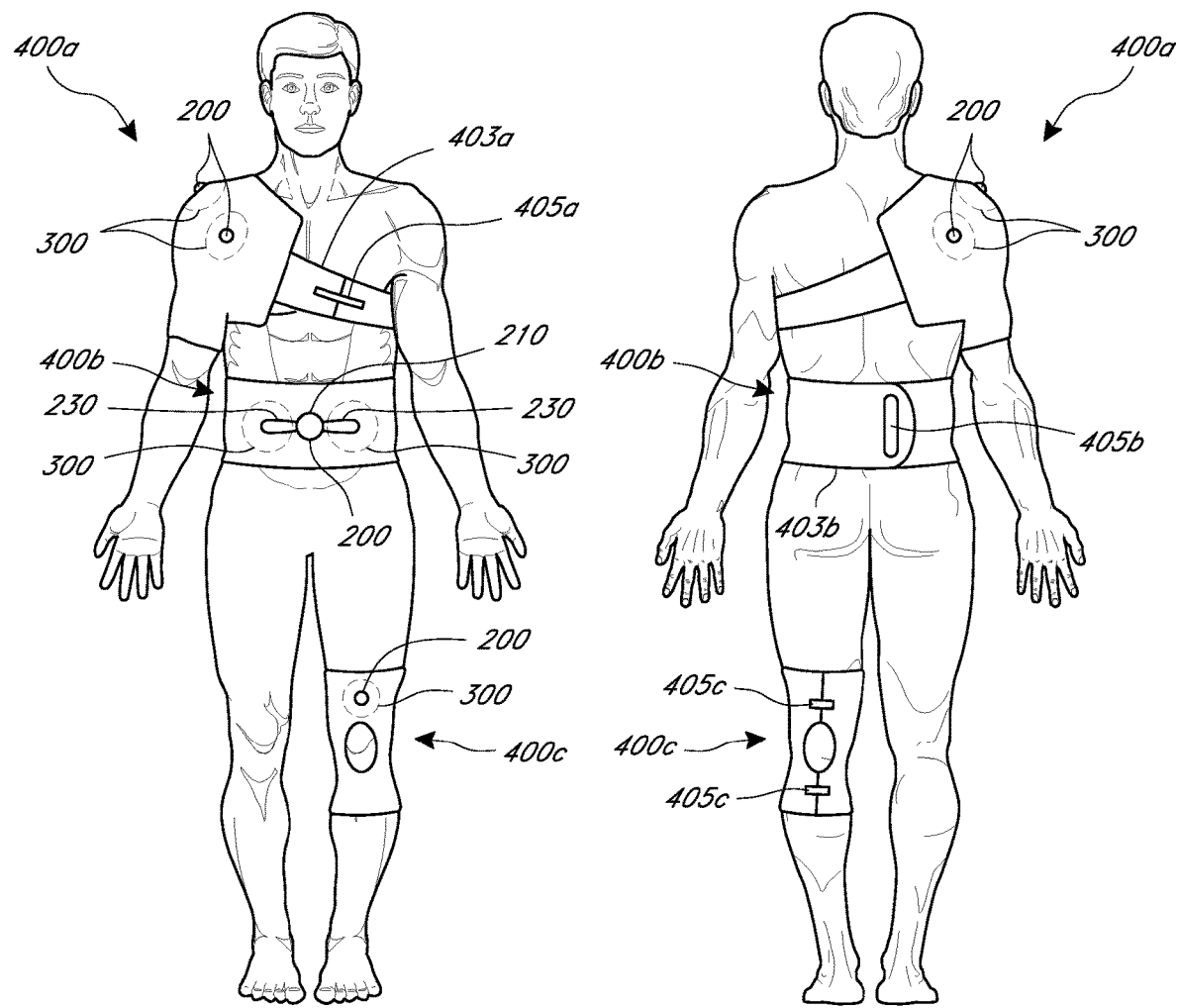

FIGS. 7A and 7B show front and back views of a user wearing several embodiments of garments including electrical stimulation devices. While the user is illustrated as wearing three garments, it will be understood that a user may wear only one garment or other combinations of garments than those shown. Garment 400a is configured for use on a user's shoulder and includes three electrodes 300, each with a gel dispensing system 200. Other numbers of electrodes and gel dispensing systems and other placements on the garment 400a are possible. The garment 400a fits over a user's shoulder and positions the electrodes 400 on the body. The garment 400a includes a strap 403a which is secured with a closure mechanism 405a. A closure mechanism may include buckles, clasps, snaps, ties, laces, hook and loop, or any other type of mechanism for securing the garment. Garment 400b is configured for use on a user's abdominal region. The garment 400b is configured as a strap 403b which extends around the user's torso and is secured with a closure mechanism 405b. In the illustrated embodiment, the garment 400b includes two electrodes 300 and a gel dispensing system 200. The gel dispensing system 200 includes a reservoir 210 and two fluid passageways 230 for delivering the gel or liquid to the electrodes 300. Other numbers of electrodes, gel dispensing systems, and their placement on the garment are possible. Garment 400c is configured for use on a user's knee. The garment 400c is configured to wrap around a user's knee and is secured with one or more closure mechanisms 405c. In the illustrated embodiment, the garment 400c includes an electrode 300 and gel dispensing system 200 positioned above the user's knee. Other numbers of electrodes, gel dispensing systems, and their placement on the garment are possible.

Figures 7C, 7D:
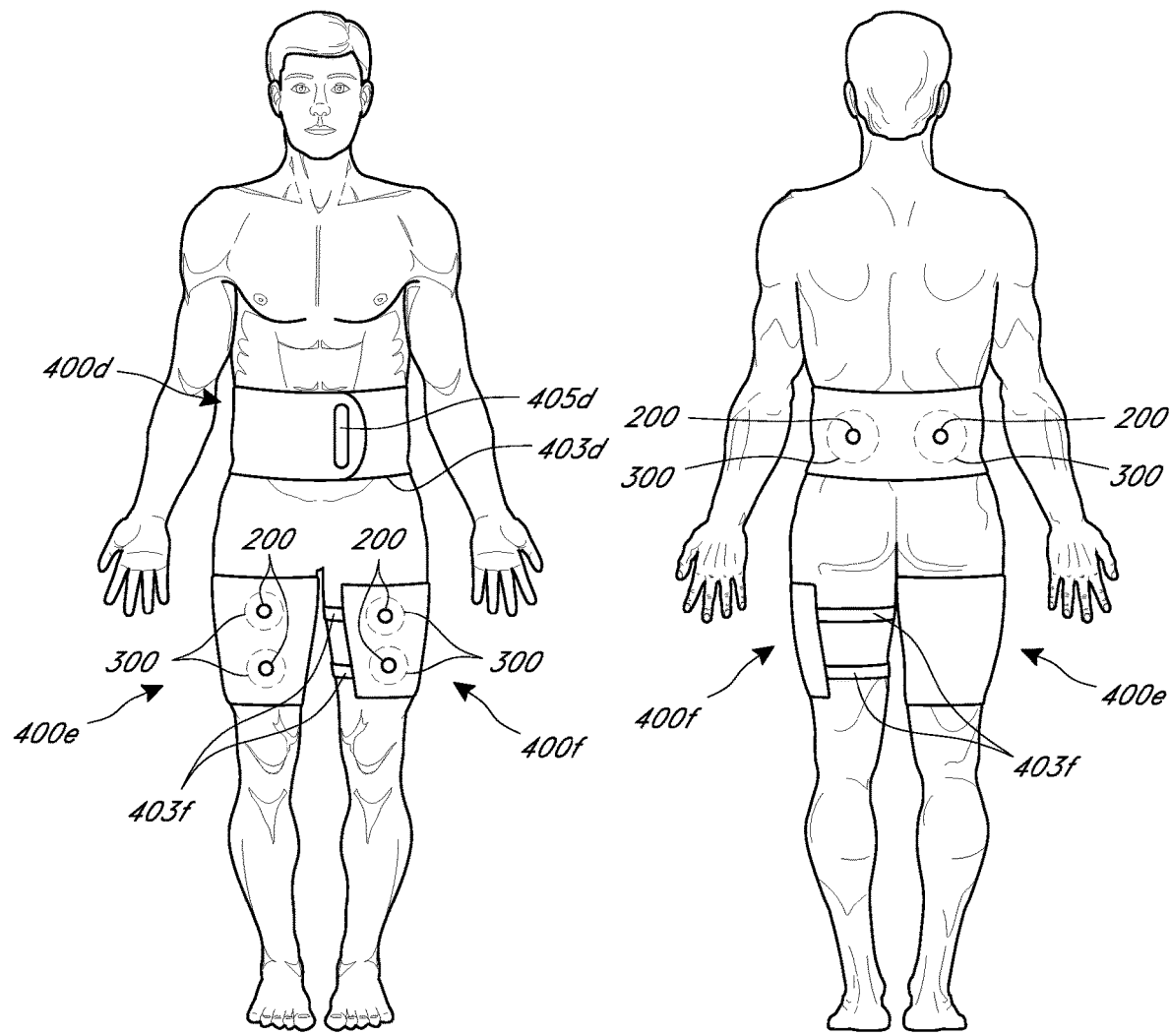

FIGS. 7C and 7D show front and back views of a user wearing several additional embodiments of garments including electrical stimulation devices. While the user is illustrated as wearing three garments, it will be understood that a user may wear only one garment or other combinations of garments than those shown. Garment 400d is configured for user on a user's lower back. It is configured as a strap 403d which extends around a user's torso and is secured with a closure mechanism 405d. In the illustrated embodiment, the garment 400d includes two electrodes 300 and two fluid dispensing systems 200. However, other numbers of electrodes, gel dispensing systems, and their placement on the garment are possible. Garment 400e is configured for use on a user's thigh, it is configured as a sleeve which extends around the thigh. The sleeve is donned by inserting a user's foot through the sleeve and sliding the sleeve up the leg until it is positioned on the thigh. The garment 400e is illustrated with two electrodes 300 and two fluid dispensing systems 200. However, other numbers of electrodes, gel dispensing systems, and their placement on the garment are possible. Garment 400f is also configured for use on a user's thigh. However, it is configured to be secured to the thigh with straps 403f. In the illustrated embodiment, the garment 400f includes two electrodes 300 and two fluid dispensing systems 200. However, other numbers of electrodes, gel dispensing systems, and their placement on the garment are possible.

FIGS. 7E and 7F show front and back views of a user wearing several additional embodiments of garments including electrical stimulation devices. While the user is illustrated as wearing two garments, it will be understood that a user may wear only one garment or other combinations of garments than those shown. Garment 400g is configured generally as a shirt with embedded electrodes 300 and gel dispensing systems 200. The garment 400g may be configured to fit tightly against a user's body so as to cause the electrodes 300 to contact the body. In the illustrated embodiment, the garment 400g includes electrodes positioned over the user's abdominal region (FIG. 7E) and electrodes positioned over the user's lower back region (FIG. 7F). However, in some embodiments, the garment 400g may include only one or the other. Further, the numbers and placement of the electrodes 300 and gel dispensing systems 200 are provided by way of example only and may be varied as desired. Garment 400f is configured generally as shorts or pants with embedded electrodes 300 and gel dispensing systems 200. The garment 400g may be configured to fit tightly against a user's body so as to cause the electrodes 300 to contact the body. In the illustrated embodiment, the garment 400g includes electrodes positioned over the user's right and left knees. However, in some embodiments, the garment 400g may include only electrodes positioned over one or the other. Further, the numbers and placement of the electrodes 300 and gel dispensing systems 200 are provided by way of example only and may be varied as desired.

Figure 7G:
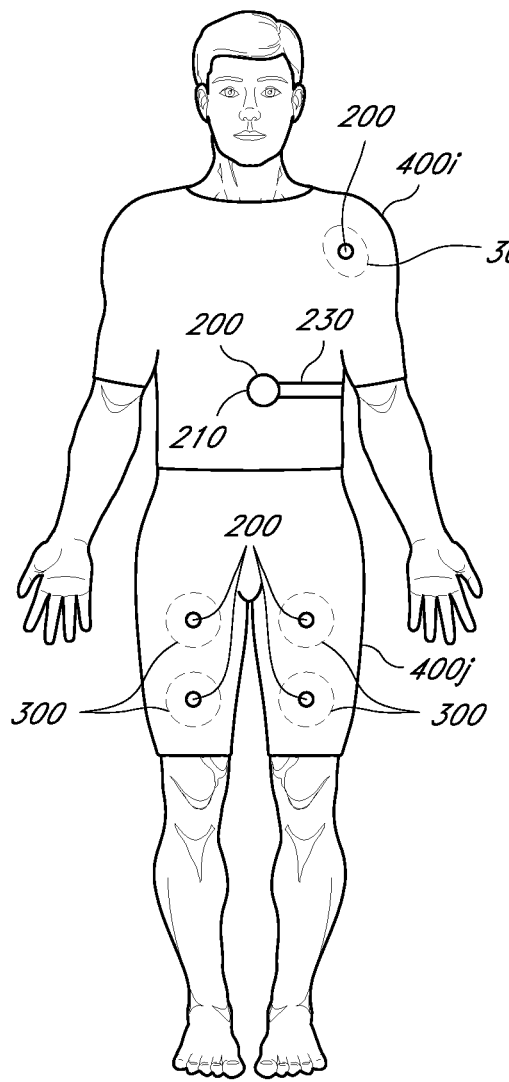
Figure 7H:
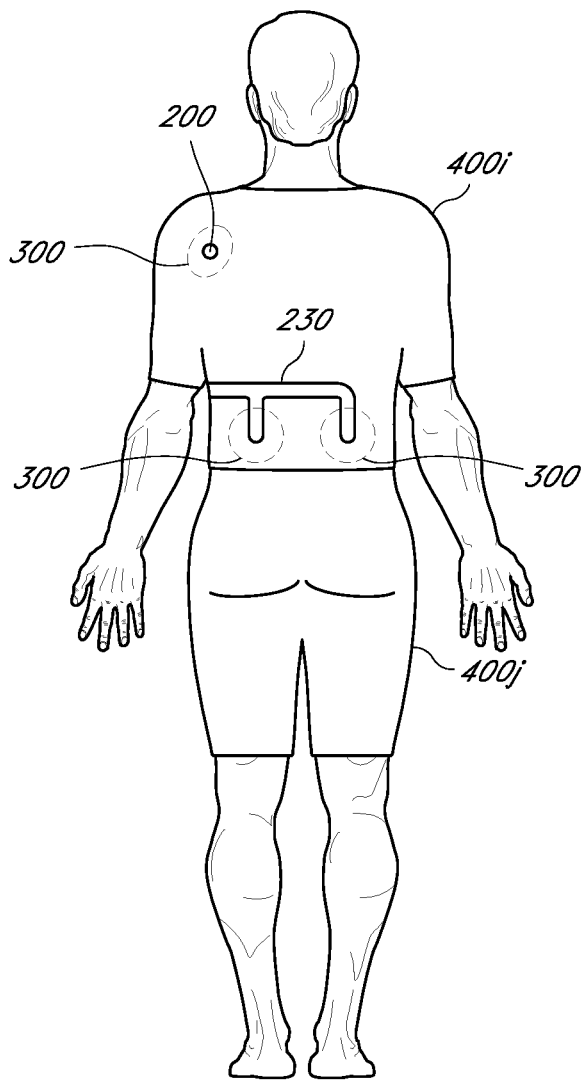

FIGS. 7G and 7H show front and back views of a user wearing several additional embodiments of garments including electrical stimulation devices. While the user is illustrated as wearing two garments, it will be understood that a user may wear only one garment or other combinations of garments than those shown. Garment 400i is configured generally as a shirt with embedded electrodes 300 and gel dispensing systems 200. The garment 400g may be configured to fit tightly against a user's body so as to cause the electrodes 300 to contact the body. In the illustrated embodiment, the garment 400g includes electrodes positioned over the user's shoulder region (FIGS. 7G and 7H) and electrodes positioned over the user's lower back region (FIG. 7H). However, in some embodiments, the garment 400g may include only one or the other. Further, the numbers and placement of the electrodes 300 and gel dispensing systems 200 are provided by way of example only and may be varied as desired. In the illustrated embodiment, the electrodes 300 positioned on the user's lower back are connected to a gel dispensing system 200 which is positioned on the front of the garment for ease of access. The gel dispensing system 200 includes a reservoir 210 which is connected to the electrodes 300 by a branched fluid passageway 230. The fluid passageway 230 may extend over the garment, under the garment, or through the garment. Garment 400j is configured generally as shorts or pants with embedded electrodes 300 and gel dispensing systems 200. The garment 400j may be configured to fit tightly against a user's body so as to cause the electrodes 300 to contact the body. In the illustrated embodiment, the garment 400g includes electrodes positioned over the user's right and left thighs. However, in some embodiments, the garment 400g may include only electrodes positioned over one or the other. Further, the numbers and placement of the electrodes 300 and gel dispensing systems 200 are provided by way of example only and may be varied as desired.

Again, the garments illustrated in FIGS. 7A through 7H are provided by way of example only. Various modifications to these examples will be apparent to those skilled in the art and are within the scope of this disclosure. Features from any of the illustrated embodiments may be modified and combined with any of the features from the other illustrated embodiments. The gel dispensing systems 200 and electrodes 300 shown in FIGS. 7A through 7H may include any of the features discussed throughout this disclosure, including those discussed in reference to FIGS. 1A through 6B.

Figure 8:
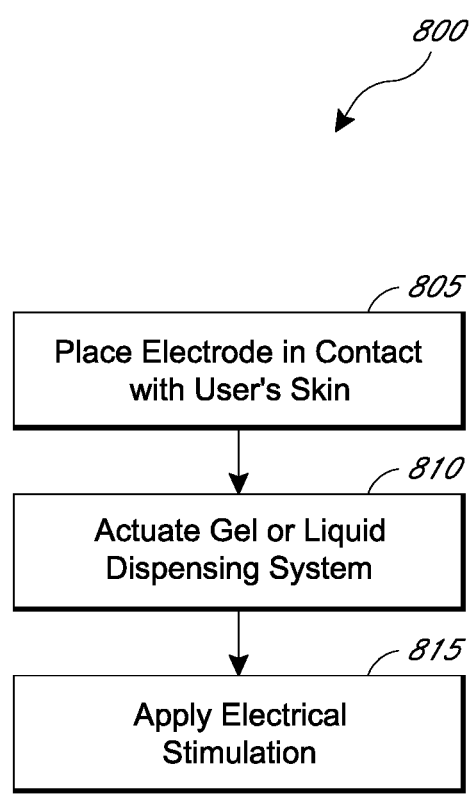
FIG. 8 is a flow chart illustrating a method of using an electrical stimulation device.

FIG. 8 is a flow chart illustrating a method 800 of using an electrical stimulation device, such as electrical stimulation device 100 or any other electrical stimulation device configured according to the principles of the present disclosure. The method 800 begins at block 805 with placing a surface of an electrode in contact with a user's skin. In some embodiments, placing the surface of the electrode in contact with a user's skin includes donning a garment wherein the electrode is embedded. At block 810, a gel or liquid dispensing system is actuated to dispense a gel or liquid onto the surface of the electrode. In some embodiments, this may be performed with the gel dispensing systems described herein while the surface of the electrode is in contact with the user's skin. At block 815, the method further includes applying an electrical stimulation to the user via the electrode. The method 800 or individual steps of the method 800 may be repeated as desired. For example, after a period of use, the user may reapply gel or liquid to the electrode using the gel dispensing system, without removing or repositioning the electrode.

Although the preceding disclosure has been described in terms of electrical stimulation devices, the invention need not be limited to only that application. For example, garments including electrodes and gel dispensing systems as described above can be used in many sensing, testing, diagnostic, or monitoring applications, such as, for example, electrocardiography. In these embodiments, the electrodes may be connected to patient monitors that measure and/or record sensed electrical signals. An integrated gel dispensing system as described herein can be included for use with these sensing electrodes. In general, the preceding disclosure may be applied wherever electrodes that can be used with a conductive gel or liquid are used. The disclosure has particular application to embodiments that include reusable electrodes integrated into garments.

The foregoing description details certain embodiments of the systems, devices, and methods disclosed herein. It will be appreciated, however, that no matter how detailed the foregoing appears in text, the systems, devices, and methods can be practiced in many ways. As is also stated above, it should be noted that the use of particular terminology when describing certain features or aspects of the invention should not be taken to imply that the terminology is being re-defined herein to be restricted to including any specific characteristics of the features or aspects of the technology with which that terminology is associated.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about,' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A device for electrical stimulation of a user, the device comprising:
    an electrode having a first side attached to a first side of a garment and having a second side, opposite the first side for contacting a portion of a user's skin when the garment is worn by the user, wherein the electrode comprises surface features, formed on the second side of the electrode to distribute a gel or liquid across the surface of the electrode; and
    a gel or liquid dispensing system attached to the garment and configured to be actuatable to dispense a gel or liquid onto the second side of the electrode, the dispensing system comprising
    a reservoir configured to hold the gel or liquid, the reservoir having a compressible bubble shaped surface positioned on a second side of the garment directly opposite the electrode, the bubble shaped surface of the reservoir comprising a pressure deformable material extending away from the second side of the garment; and
    a fluid passageway extending straight from the reservoir through the garment and through the electrode to the second side of the electrode, wherein the reservoir and the fluid passageway are collectively configured to deliver the gel or liquid through the passageway and onto the second side of the electrode when the bubble shaped surface of the reservoir is deformed.

2. The device of claim 1, wherein the dispensing system is attached to the second side of the garment, the second side opposite the first side, and wherein the fluid passageway extends through an opening in the garment.

3. The device of claim 1, further comprising a valve positioned in the fluid passageway.

4. The device of claim 3, wherein the valve is a one-way valve configured to allow the gel or liquid to flow in only a direction from the reservoir to the electrode.

5. The device of claim 1, wherein the reservoir is refillable.

6. The device of claim 5, wherein the reservoir further comprises an inlet port configured for refilling the reservoir.

7. The device of claim 6, wherein the reservoir is configured to receive pre-filled packets of the gel or liquid.

8. The device of claim 1, wherein the reservoir is selectively attachable to the garment.

9. The device of claim 1, wherein the electrode comprises carbon.

10. The device of claim 1, wherein the pressure deformable material comprises a thin plastic material.

11. The device of claim 1, wherein the pressure deformable material comprises a rubber material.

12. The device of claim 1, where the electrode comprises carbon.

13. The device of claim 1, wherein the electrode comprises a carbon equivalent.

14. The device of claim 1, wherein the reservoir is further configured to receive a pre-filled packet of gel or liquid, the reservoir further comprising:
    a base portion,
    a movable portion attached to the base portion by a hinge and configured to move between an open position and a closed position, in the closed position the movable portion and the base portion defining an interior volume,
    a port positioned within the interior volume and configured to mate with a corresponding port on the packet, and
    wherein the movable portion includes the deformable material, and wherein the dispensing system is configured to be actuated by applying pressure to the deformable material.

* * * * *